United States Patent
Bergveld et al.

(10) Patent No.: US 6,463,312 B1
(45) Date of Patent: Oct. 8, 2002

(54) MICRODIALYSIS-PROBE INTEGRATED WITH A SI-CHIP

(75) Inventors: Piet Bergveld, Haarboerhorst (NL); Sebastian Bohm, Gb Enschede (NL); Wouter Olthuis, Gl Enschede (NL)

(73) Assignee: Stichting Voor Fundamenteel Onderzoek der Materie, Utrecht (NL)

( * ) Notice: Subject to any disclaimer, the term of this patent is extended or adjusted under 35 U.S.C. 154(b) by 0 days.

(21) Appl. No.: 09/601,873
(22) PCT Filed: Feb. 4, 1999
(86) PCT No.: PCT/NL99/00057
§ 371 (c)(1), (2), (4) Date: Sep. 12, 2000
(87) PCT Pub. No.: WO99/41606
PCT Pub. Date: Aug. 19, 1999

(30) Foreign Application Priority Data

Feb. 16, 1998 (NL) .............................................. 1008315

(51) Int. Cl.⁷ ................................................. A61B 5/05
(52) U.S. Cl. ........................ 600/345; 600/309; 600/347
(58) Field of Search ................................ 600/345, 347, 600/307; 604/4.01, 5.01–5.04, 6.01–6.06, 6.09–6.11, 6.16

(56) References Cited

U.S. PATENT DOCUMENTS

| 5,165,406 A | * 11/1992 | Wong ........................... 600/345 |
| 5,591,139 A | * 1/1997 | Lin et al. ..................... 604/264 |
| 5,640,954 A | * 6/1997 | Pfeiffer et al. ............... 600/345 |

\* cited by examiner

Primary Examiner—Robert L. Nasser
Assistant Examiner—Patricia C. Mallari
(74) Attorney, Agent, or Firm—Michael D. Bednarek; Shaw Pittman LLP

(57) ABSTRACT

Microdialysis device (10), comprising at least a probe (1) provided with an inlet (2) and an outlet (3) for bringing a perfusion fluid into contact with a bodily fluid in a part of a living organism and causing constituents from this fluid to be taken up by this perfusion fluid, whereby the perfusion fluid is enriched to dialysate, wherein the outlet (3) is integrally received in a silicon chip (5) and debouches in a first fluid channel (6) formed in this silicon chip (5) and wherein further at least one analysis means, for instance an ISFET (17, 18), for analysing constituents of the bodily fluid taken up by the perfusion fluid is integrally received in the silicon chip (5) in a manner such that dialysate flowing from the outlet (3) comes into contact with said analysis means in the first fluid channel (6), and wherein the silicon chip (5) is further optionally provided with pumping means (50) or dosing means.

9 Claims, 3 Drawing Sheets

MICRODIALYSIS-PROBE INTEGRATED WITH A SI-CHIP

Figure 1:
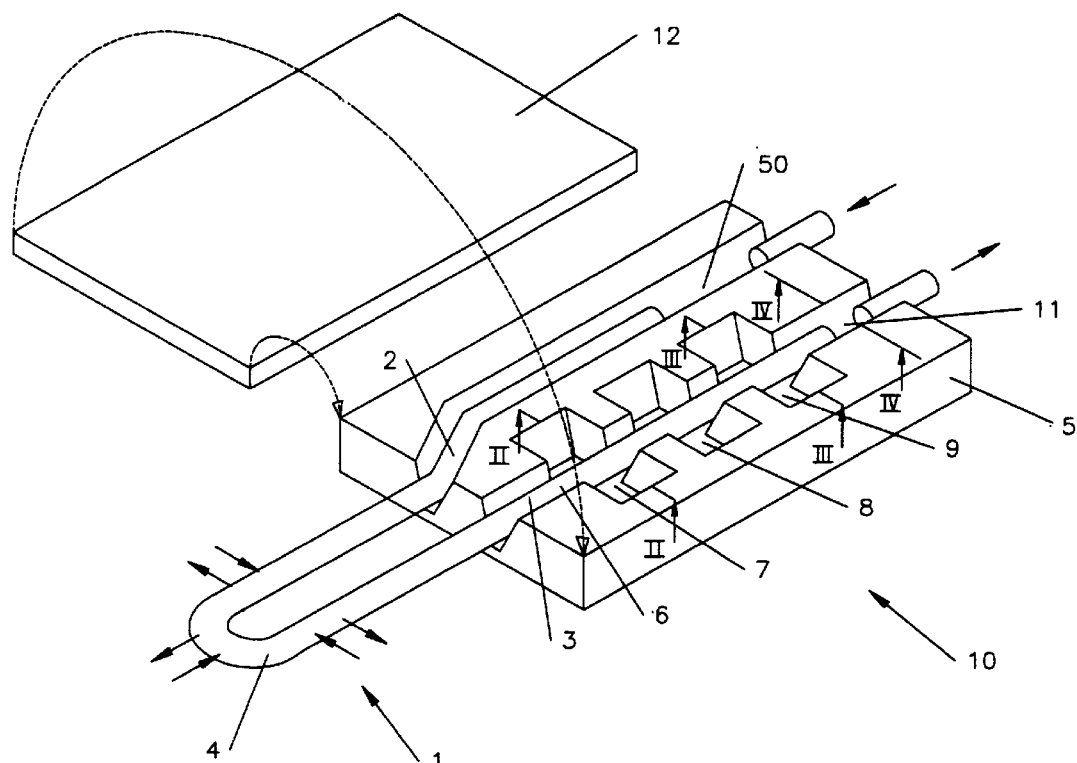

The invention relates to a microdialysis device comprising at least a probe provided with an inlet and an outlet for bringing a perfusion fluid into contact with a bodily fluid in a part of a living organism and causing constituents from this fluid to be taken up by this perfusion fluid, whereby the perfusion fluid is enriched to dialysate.

Such a device is known from the U.S. Pat. No. 5,640,954. The device known from this patent relates to a method and a device for continuously monitoring the concentration of a metabolite, such as a glucose or lactic acid, in biological tissue, in which a perfusion fluid is guided to a microdialysis probe implanted in the subcutaneous tissue and is discharged therefrom as dialysate after enrichment with the metabolites from the tissue fluid. According to the described method an enzyme is added to the dialysate, and the concentration of the metabolite in the dialysate is determined under the selective effect of the enzyme at a measuring point ex vivo, making use of an electrochemical sensor.

It is a drawback of the known microdialysis device that for analysis of the constituents taken up in the perfusion fluid, although performed on-line, use is made of relatively voluminous conventional analytical equipment which limits the clinical application of the microdialysis technique. This analysis equipment must be connected using tubes and adaptors to the microdialysis probe, the flow rate of which is exceptionally small (in the order of magnitude of microlitres per minute). The resulting dead volume in combination with the extremely small samples for analysis represents a problem. It is further a drawback of the known device that connecting of the separate components thereof using hoses and coupling pieces does not preclude the possibility of errors being made by an operator. It is a further drawback that the known device is in principle suitable for performing an analysis of only a determined constituent, because the addition of enzyme makes the dialysate unsuitable for analysis of other constituents.

It is an object of the invention to provide a microdialysis device with which extremely small quantities of dialysate can be analysed in reliable manner with a negligible waiting time, wherein a plurality of constituents can be determined and wherein the possibility of an operator making errors is virtually precluded.

According to the invention a microdialysis device of the type stated in the preamble is proposed for this purpose, wherein the outlet of the probe is integrally received in a silicon chip and debouches in a first fluid channel formed in this silicon chip.

Such a device for microdialysis not only provides the advantage that the dead volume is significantly smaller than in a device according to the prior art, but also provides the possibility of integral arrangement in the silicon chip or in the housing thereof of vulnerable junctions in the fluid conduits to and from the probe.

In an advantageous embodiment of a microdialysis device according to the invention, which further comprises analysis means for analysing constituents of the bodily fluid taken up by the perfusion fluid, at least one analysis means is integrally received in the silicon chip in a manner such that dialysate flowing from the outlet comes into contact with this analysis means in the first fluid channel.

In one embodiment the at least one analysis means comprises a sensor, for instance an ion-sensitive field effect transistor (ISFET).

In a further embodiment the at least one analysis means comprises a fluid reservoir in the silicon chip, via which reservoir constituents from the dialysate come into contact with a sensor received in this reservoir, or which reservoir for instance contains a calibration fluid with constituents for adding to the dialysate in the first fluid channel.

The presence of particular substances in the dialysate and, in combination with a fluid reservoir containing a calibration substance, also the concentration of these determined substances is determined using a sensor.

The fluid reservoir is for instance separated by a semi-permeable membrane from the first fluid channel, or for instance contains a gelled fluid, wherein the first fluid channel comprises a cavity formed in the gelled fluid.

In another embodiment the at least one analysis means comprises a fluid reservoir which is provided with a layered structure of a precious metal and a salt derived from that precious metal and which contains an electrolytic solution. A reference electrode integrated into the silicon chip is thus provided which can for instance be used as counter electrode of a sensor for a potentiometric measurement, for instance a pH measurement, of dialysate flowing through the fluid channel.

In yet another embodiment the silicon chip is provided with pumping means for pumping the perfusion fluid respectively the dialysate.

In an advantageous embodiment the pumping means are adapted for intermittent pumping of the perfusion fluid respectively the dialysate.

Intermittent pumping provides the option of holding the perfusion fluid in a probe introduced into a part of an organism at the same location for some time, until in an equilibrium situation constituents from the bodily fluid are taken up in the perfusion fluid, for instance by diffusion through a semi-permeable part of the probe at that location. The thus formed dialysate can subsequently be pumped to a sensor present in the silicon chip, where the dialysate can be kept in contact with this sensor for a chosen, sufficiently long period. This offers the advantage that sensors become available which would be unsuitable in the case of a measurement with non-intermittent pumping means due to these sensors having too long a response time.

The pumping means for instance comprise at least one closed reservoir which is filled with a reversibly expandable medium and is provided with an actuator for this medium, which reservoir is provided on one side with a movable wall part. When this movable wall part also forms part of a conduit for perfusion fluid or dialysate, the moving wall part, optionally in combination with suitably chosen and placed valves in this conduit, can be utilized for pumping the relevant fluid through this conduit.

The expandable medium expands in a physical or physical-chemical process, preferably in reversible manner, for instance as a function of the temperature.

In an advantageous embodiment the expandable medium expands as a function of the pH, wherein the reservoir is provided with electrodes. Using these electrodes the pH of the expandable medium is changed in coulometric manner.

In a subsequent embodiment the silicon chip is provided with dosing means for dosing an additive in the perfusion fluid respectively the dialysate.

These dosing means for instance comprise at least a second fluid channel which is provided at a first, closed outer end with electrodes and which debouches with a second, open outer end in a fluid channel.

Using the dosing means small quantities of fluid (for instance calibration fluid or reagents) can be dosed in accurate manner in very small quantities (in the order of nanolitres) into the first fluid channel in the silicon chip.

It is otherwise noted that the application of pumping means or dosing means according to the invention is not limited to systems for microdialysis. The dosing means are for instance particularly suitable for subcutaneous administration with a syringe of medication such as painkillers.

In an advantageous embodiment the inlet of the probe is also integrally received in the silicon chip.

In a preferred embodiment of a microdialysis device according to the invention, wherein the probe comprises two substantially concentric tubes, of which an inner tube comprises a portion protruding from a distal end of the outer tube, which portion is enclosed by a semi-permeable membrane connecting to the outer tube, wherein between the inner and the outer tube a through-flow channel is present, the silicon chip is provided with a first hole which extends in longitudinal direction and is formed successively by a first segment, a transition segment, a second segment and a third segment, wherein the inner periphery of the first segment corresponds with the outer periphery of said outer tube and the inner periphery of the second segment corresponds with the outer periphery of said inner tube, a second hole debouching in the transition segment and extending in substantially transverse direction and a third hole debouching in the third segment, wherein the outer tube is received with a proximal end portion in the first segment, and a portion of the inner tube protruding from the proximal end of the outer tube is received in the second segment in a manner such that the first hole is in communication with the through-flow channel between the inner and outer tube and the third hole is in communication with the interior of the inner tube.

The invention will now be further elucidated hereinbelow on the basis of embodiments with reference to the annexed drawings.

Figure 2:
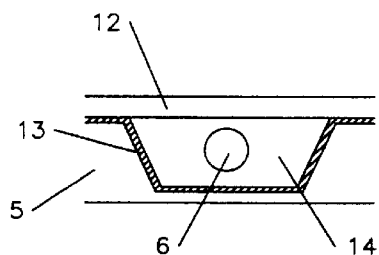
Figure 3:
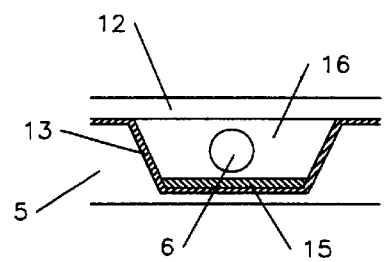
Figure 4:
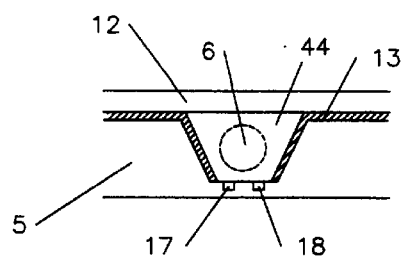
Figure 5:
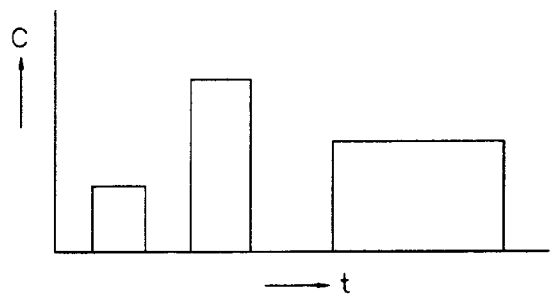
Figure 6:
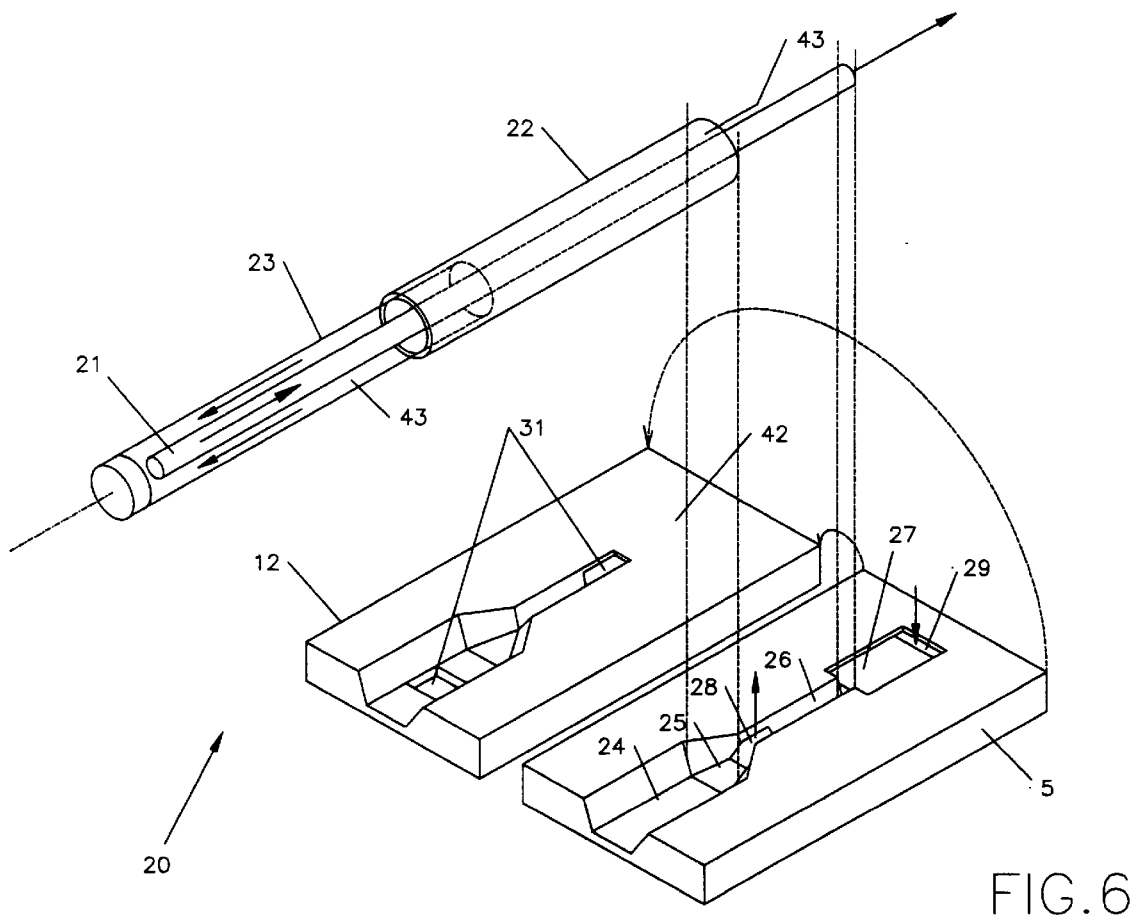
Figure 7:
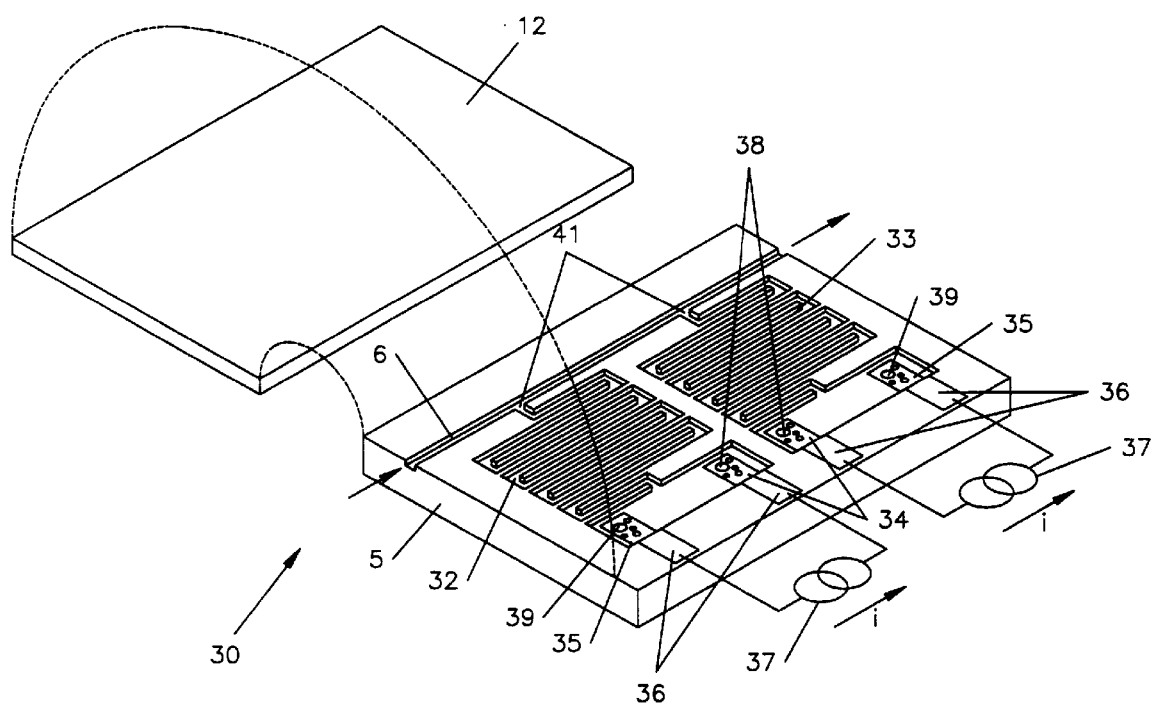

FIG. 1 is a schematic view in perspective of a first embodiment of a microdialysis device according to the invention, FIG. 2, FIG. 3 and FIG. 4 show a cross-section through details of the device of FIG. 1, FIG. 5 is a graphic representation of a measuring result obtained with a device as according to FIG. 1, FIG. 6 shows a schematic view of a cut-away second embodiment of a microdialysis device according to the invention, and FIG. 7 is a schematic view in perspective of a dosing system for a microdialysis device.

Corresponding components are designated in the drawings with the same reference numerals.

FIG. 1 shows an integrated microdialysis measuring system 10 according to the invention, in which a probe 1 is integrally received in a silicon chip 5 which is covered by a cover 12. Probe 1 consists of a U-shaped tube 4 of semi-permeable membrane which is introduced into the tissue of a body for examining and, in the line of the legs of U-shaped tube 4, inlet and outlet portions 2, 3 respectively which are integrally received in silicon chip 5. The U-shaped tube 4 is for instance a tube with a diameter of about 100 $\mu$m and a wall thickness of about 10 $\mu$m manufactured from a cellulose-acetate or a polycarbonate. The arrows on the right of the figure indicate the flow direction of the perfusion fluid respectively the dialysate through probe 1, the arrows on the left of the figure represent the take-up in the perfusion fluid of constituents from the tissue fluid. A (schematically shown) pump 50 for pumping the perfusion fluid in the indicated flow direction is integrally received in silicon chip 5 in front of the inlet 2 of the U-shaped tube 4. Outlet 3 of U-shaped tube 4 continues on as fluid channel 6 through silicon chip 5 and successively passes two reservoirs 7, 8, a reference electrode 9 and a sensor 11.

FIG. 2 shows a cross-section through silicon chip 5 of FIG. 1 along the line II—II. This shows how reservoir 7 is formed by a cavity in silicon chip 5 which is coated with a layer 13 of silicon oxide ($SiO_2$) or a sandwich of silicon oxide and silicon nitride ($SiO_2/Si_3N$) and is filled with a gel 14 containing a known concentration of a substance for analysis, which gel 14 is in contact via the semi-permeable membrane of fluid channel 6 with the dialysate guided through the measuring system.

FIG. 3 shows a cross-section along line III—III of FIG. 1 through reference electrode 9. This latter consists of a cavity in silicon chip 5 which is coated with a silver/silver chloride layer 15 (Ag/AgCl) and which is filled with a solution 16 of potassium chloride (KC1), which solution is in via the semi-permeable membrane of fluid channel 6 with the dialysate flowing through silicon chip 5. By filling cavity 16 not with KC1 but with for instance a solution with a suitably chosen so-called ion-exchanger or an ionophore (a substance which can very specifically bind molecules or ions) or with a carrier material such as polyvinyl chloride or a silicon rubber enriched with an ion-exchanger or an ionophore, an ion-specific electrode 9 is obtained.

FIG. 4 is a cross-section through sensor 11 of FIG. 1 along line IV—IV. Sensor 11 consists of a cavity 44 in the silicon chip 5 which is coated with a layer 13 of silicon oxide ($SiO_2$), through which cavity 44 runs the fluid channel 6. Formed in the bottom of cavity 44 are the source and drain 17, 18 respectively of an ion-sensitive field effect transistor (ISFET) which are in via a fluid in cavity 44 and the semi-permeable membrane of fluid channel 6 with the dialysate in fluid channel 6. The sensitivity of the ISFET can be influenced by the choice of the fluid in cavity 44. In alternative embodiments of sensor 11 the semi-permeable wall of fluid channel 6 is absent at the location of cavity 44 and the ISFET is in direct contact with the dialysate in fluid channel 6, or cavity 44 is filled with a gel, wherein the fluid channel for the dialysate is formed by a cavity 6 in this gel.

When reservoirs 7 and 8 of measuring system 10 are filled for instance with a lactic acid solution of differing concentration and sensor 11 is suitably chosen, an on-line measuring system is available for the lactic acid concentration in the tissue fluid. For a determination the U-shaped portion 4 of probe 1 is inserted into the relevant tissue respectively bodily fluid and the probe is completely filled with perfusion fluid, which in a stationary situation then takes up lactic acid molecules via the semi-permeable membrane from respectively the tissue fluid, the calibration fluid in reservoir 7 and the calibration fluid in reservoir 8. After a time the thus formed dialysate is subsequently driven along in the direction of the arrows on the right of the figure using pumping means (not shown) and a concentration-dependent signal is generated by sensor 11 as a function of the time.

FIG. 5 shows the signal of sensor 11 in the above example, wherein the right-hand block represents the signal which is proportional to the known concentration in the fluid in reservoir 8, the middle block represents the signal proportional to the known concentration in the fluid in reservoir 7 and the left-hand block represents the signal proportional to the unknown concentration in the tissue fluid. The value of the concentration of the tissue fluid can be determined in simple manner by interpolation from the two known concentrations.

FIG. 6 shows an exploded view of a measuring system 20 with a silicon chip 5 in which a hole is formed in longitudinal direction using micromachining techniques (anisotropic or isotropic etching of silicon), which hole consists successively of a first segment 24, a transition segment 25, a second segment 26 and a third segment 27. In addition, a second hole 28 is formed which debouches in transition segment 25 and a third hole 29 which debouches in third segment 27. In the hexagonal first segment 24 thus formed by anisotropic etching an outer tube 22 of a probe is placed up to the transition portion 25 and an inner tube 21 is placed in second segment 26 through outer tube 22, wherein the proximal end of inner tube 21 debouches in the third segment 27 of the channel in a manner such that between inner tube 21 and outer tube 22 a through-flow channel 43 is created which communicates with the transverse hole 28 in transition segment 25, and inner tube 21 communicates at its proximal end with third hole 29 via third segment 27. On the distal end of outer tube 22 a semi-permeable membrane 23 is formed round the portion of inner tube 21 protruding from the distal end of outer tube 22, which semi-permeable membrane 23 is closed on the distal end. The structure is made liquid-tight using a suitable adhesive which is introduced via adhesive holes 31 in cover 12. The distal end of the integrated microdialysis probe 20 with the semi-permeable membrane 23 is inserted into the tissue for examining, whereafter perfusion fluid is introduced via transverse hole 28, transition segment 25 and through-flow channel 43 (represented by the light arrows), whereafter in the tissue take-up of constituents from the tissue fluid into the perfusion fluid takes place through semi-permeable membrane 23, whereafter the fluid enriched to dialysate is subsequently discharged via inner tube 21, third segment 27 and third hole 29. The third segment 27 functions as fluid channel in which according to the invention analysis means (which are not shown but are formed for instance in sensor surface 42) are integrally received. In the shown integrated probe 20 all critical connection points are accommodated within the silicon chip, so that the probe is less vulnerable than the probes of the prior art and can moreover be used in very simple manner. In addition, the dead volume in this probe has been reduced by about 90% relative to the dead volume in known probes.

FIG. 7 shows a dosing system 30 integrated into a silicon chip 5 for adding two fluids to a dialysate flowing through a channel 6 as according to the arrows on the left and right in the figure. The dosing system comprises two meandering channels 32, 33 which are filled with the fluids for dosing and which are each provided on a first, closed outer end with electrodes 34, 35 and which debouch with a second, open outer end 41 in fluid channel 6. The fluids are pressed out of channels 32, 33 by gas bubbles 38, 39 which originate at electrodes 34, 35 when a current is passed through these electrodes via terminals 36 using a power source 37.

What is claimed is:

1. Microdialysis device (10, 20), comprising at least a probe (1) provided With an inlet (2) and an outlet (3) for bringing a perfusion fluid into contact with a bodily fluid in a part of a living organism and causing constituents from this fluid to be taken up by this perfusion fluid, whereby the perfusion fluid is enriched to dialysate, further comprising analysis means (7, 8, 9, 11) for analysing constituents of the bodily fluid taken up by the perfusion fluid, wherein the outlet (3) of the probe (1) is integrally received in a silicon chip (5) and debouches in a first fluid channel (6) formed in this silicon chip (5), and at least one analysis means comprising a fluid reservoir (7, 8, 9, 44) is integrally received in the silicon chip (5) in a manner such that dialysate flowing from the outlet (3) comes into contact with said analysis means in the first fluid channel (6), the silicon chip (5) being provided with pumping means (50) for pumping the perfusion fluid respectively the dialysate, characterized in that the pumping means (50) comprise at least one closed reservoir which is filled with a reversibly expandable medium and is provided with an actuator for the expansion of this medium, which reservoir is closed on one side by a movable wall part.

2. Microdialysis device as claimed in claim 1, characterized in that the expandable medium expands as a function of the pH and the reservoir is provided with electrodes.

3. Microdialysis device (10, 20), comprising at least a probe (1) provided with an inlet (2) and an outlet (3) for bringing a perfusion fluid into contact with a bodily fluid in a part of a living organism and causing constituents from this fluid to be taken up by this perfusion fluid, whereby the perfusion fluid is enriched to dialysate, further comprising analysis means (7, 8, 9, 11) for analysing constituents of the bodily fluid taken up by the perfusion fluid, wherein the outlet (3) of the probe (1) is integrally received in a silicon chip (5) and debouches in a first fluid channel (6) formed in this silicon chip (5), and at least one analysis means comprising a fluid reservoir (7, 8, 9, 44) is integrally received in the silicon chip (5) in a manner such that dialysate flowing from the outlet (3) comes into contact with said analysis means in the first fluid channel (6), characterized in that the silicon chip (5) is provided with dosing means (30) for dosing an additive into the perfusion fluid or into the dialysate.

4. Microdialysis device (10, 20), comprising at least a probe (1) provided with an inlet (2) and an outlet (3) for bringing a perfusion fluid into contact with a bodily fluid in a part of a living organism and causing constituents from this fluid to be taken up by this perfusion fluid, whereby the perfusion fluid is enriched to dialysate, further comprising analysis means (7, 8, 9, 11) for analysing constituents of the bodily fluid taken up by the perfusion fluid, wherein the outlet (3) of the probe (1) is integrally received in a silicon chip (5) and debouches in a first fluid channel (6) formed in this silicon chip (5), and at least one analysis means comprising a fluid reservoir (7, 8, 9, 44) is integrally received in the silicon chip (5) in a manner such that dialysate flowing from the outlet (3) comes into contact with said analysis means in the first fluid channel (6), the silicon chip (5) being provided with dosing means (30) for dosing an additive into the perfusion fluid or into the dialysate, characterized in that, that the dosing means (30) comprise at least a second fluid channel (32, 33) which is provided on a first, closed outer end with electrodes (34, 35) and which debouches with a second, open outer end (41) in the first fluid channel (6).

5. Microdialysis device (10, 20), comprising at least a probe (1) provided with an inlet (2) and an outlet (3) for bringing a perfusion fluid into contact with a bodily fluid in a part of a living organism and causing constituents from this fluid to be taken up by this perfusion fluid, whereby the perfusion fluid is enriched to dialysate, further comprising analysis means (7, 8, 9, 11) for analysing constituents of the bodily fluid taken up by the perfusion fluid, wherein the outlet (3) of the probe (1) is integrally received in a silicon chip (5) and debouches in a first fluid channel (6) formed in this silicon chip (5), and at least one analysis means comprising a fluid reservoir (7, 8, 9, 44) is integrally received in the silicon chip (5) in a manner such that dialysate flowing from the outlet (3) comes into contact with said analysis means in the first fluid channel (6), characterized in that, that the fluid reservoir (7, 8, 9) contains a gelled fluid and the first fluid channel (6) comprises a cavity formed in this gelled fluid.

6. Microdialysis device (10, 20), comprising at least a probe (1) provided with an inlet (2) and an outlet (3) for bringing a perfusion fluid into contact with a bodily fluid in a part of a living organism and causing constituents from this fluid to be taken up by this perfusion fluid, whereby the perfusion fluid is enriched to dialysate, further comprising analysis means (7, 8, 9, 11) for analysing constituents of the bodily fluid taken up by the perfusion fluid, wherein the outlet (3) of the probe (1) is integrally received in a silicon chip (5) and debouches in a first fluid channel (6) formed in this silicon chip (5), and at least one analysis means comprising a fluid reservoir (7, 8, 9, 44) is integrally received in the silicon chip (5) in a manner such that dialysate flowing from the outlet (3) comes into contact with said analysis means in the first fluid channel (6), the at least one analysis means comprising a sensor (11), the fluid reservoir (7, 8, 9) being separated from the first fluid channel (6) by a semi-permeable membrane, characterized in that the fluid reservoir (9) is provided with a layered structure (15) of a precious metal and contains a salt derived from this precious metal and a electrolytic fluid (16).

7. Microdialysis device (10, 20), comprising at least a probe (1) provided with an inlet (2) and an outlet (3) for bringing a perfuision fluid into contact with a bodily fluid in a part of a living organism and causing constituents from this fluid to be taken up by this perfusion fluid, whereby the perfusion fluid is enriched to dialysate, further comprising analysis means (7, 8, 9, 11) for analysing constituents of the bodily fluid taken up by the perfusion fluid, wherein the outlet (3) of the probe (1) is integrally received in a silicon chip (5) and debouches in a first fluid channel (6) formed in this silicon chip (5), and at least one analysis means comprising a fluid reservoir (7, 8, 9, 44) is integrally received in the silicon chip (5) in a manner such that dialysate flowing from the outlet (3) comes into contact with said analysis means in the first fluid channel (6), the at least one analysis means comprising a sensor (11), the fluid reservoir (7, 8, 9) being separated from the first fluid channel (6) by a semi-permeable membrane, being provided with a layered structure (15) of a precious metal and containing a salt derived from this precious metal and a electrolytic fluid (16), characterized in that the electrolytic fluid (16) comprises an ion exchanger.

8. Microdialysis device (10, 20), comprising at least a probe (1) provided with an inlet (2) and an outlet (3) for bringing a perfusion fluid into contact with a bodily fluid in a part of a living organism and causing constituents from this fluid to be taken up by this perfusion fluid, whereby the perfusion fluid is enriched to dialysate, further comprising analysis means (7, 8, 9, 11) for analysing constituents of the bodily fluid taken up by the perfusion fluid, wherein the outlet (3) of the probe (1) is integrally received in a silicon chip (5) and debouches in a first fluid channel (6) formed in this silicon chip (5), and at least one analysis means comprising a fluid reservoir (7, 8, 9, 44) is integrally received in the silicon chip (5) in a manner such that dialysate flowing from the outlet (3) comes into contact with said analysis means in the first fluid channel (6), the at least one analysis means comprising a sensor (11), the fluid reservoir (7, 8, 9) being separated from the first fluid channel (6) by a semi-permeable membrane, being provided with a layered structure (15) of a precious metal and containing a salt derived from this precious metal and a electrolytic fluid (16), characterized in that the electrolytic fluid (16) comprises an ionophore.

9. Microdialysis device (20), comprising at least a probe (1) provided with an inlet (2) and an outlet (3) for bringing a perfusion fluid into contact with a bodily fluid in a part of a living organism and causing constituents from this fluid to be taken up by this perfusion fluid, whereby the perfusion fluid is enriched to dialysate, further comprising analysis means (7, 8, 9, 11) for analysing constituents of the bodily fluid taken up by the perfusion fluid, wherein the outlet (3) of the probe (1) is integrally received in a silicon chip (5) and debouches in a first fluid channel (6) formed in this silicon chip (5), and at least one analysis means comprising a fluid reservoir (7, 8, 9, 44) is integrally received in the silicon chip (5) in a manner such that dialysate flowing from the outlet (3) comes into contact with said analysis means in the first fluid channel (6), and wherein the probe comprises two substantially concentric tubes, of which an inner tube (21) comprises a portion protruding from a distal end of the outer tube (22), which portion is enclosed by a semi-permeable membrane (23) connecting to the outer tube, wherein between the inner (21) and the outer tube (22) a through-flow channel (43) is present, characterized in that the silicon chip (5) is provided with a first hole which extends in longitudinal direction and is formed successively by a first segment (24), a transition segment (25), a second segment (26) and a third segment (27), wherein the inner periphery of the first segment (24) corresponds with the outer periphery of said outer tube (22) and the inner periphery of the second segment (26) corresponds with the outer periphery of said inner tube (21), a second hole (28) debouching in the transition segment (25) and extending substantially in transverse direction, and a third hole (29) debouching in the third segment (27), wherein
the outer tube (22) is received with a proximal end portion in the first segment (24), and
a portion of the inner tube (21) protruding from the proximal end of the outer tube (22) is received in the second segment (21),
in a manner such that the second hole (28) is in communication with the through-flow channel (43) between the inner (21) and outer (22) tube and the third hole (29) is in communication with the interior of the inner tube (21).

* * * * *